United States Patent [19]
Camden

[11] Patent Number: 6,136,835
[45] Date of Patent: Oct. 24, 2000

[54] METHODS OF TREATMENT FOR VIRAL INFECTIONS

[75] Inventor: James Berger Camden, West Chester, Ohio

[73] Assignee: The Procter & Gamble Company, Cincinnati, Ohio

[21] Appl. No.: 09/394,382

[22] Filed: Sep. 10, 1999

Related U.S. Application Data

[63] Continuation-in-part of application No. 09/312,948, May 17, 1999.
[51] Int. Cl.⁷ ..................................................... A61K 31/41
[52] U.S. Cl. ............................................................. 514/383
[58] Field of Search ............................................... 514/383

[56] References Cited

U.S. PATENT DOCUMENTS 5,665,751   9/1997   Camden ................................. 514/383

*Primary Examiner*—Jerome D. Goldberg
*Attorney, Agent, or Firm*—Rose and Dabek; Jacobus C. Rasser

[57] ABSTRACT

Methods for the treatment of cancers or tumors in mammals are disclosed which uses 2-(2,4-difluorophenyl)-1,3-bis(1H-1,2,4-triazol-1-yl)propan-2-ol or derivatives thereof. A chemotherapeutic agent and/or a potentiator may be used in combination with 2-(2,4-difluorophenyl)-1,3-bis(1H-1,2,4-triazol-1-yl)propan-2-ol or derivatives thereof. 2-(2,4-Difluorophenyl)-1,3-bis(1H-1,2,4-triazol-1-yl)propan-2-ol or derivatives thereof may also be used to treat viral infections, either alone, in combination with other anti-viral agents, or in combination with a potentiator.

6 Claims, No Drawings

METHODS OF TREATMENT FOR VIRAL INFECTIONS

This is a continuation-in-part of application Ser. No. 09/312,948, filed May 17, 1999, which claims priority to U.S. Ser. No. 08/674,180, filed Jul. 16, 1996 and issued as U.S. Pat. No. 5,840,742, which claims priority to U.S. Ser. No. 08/473,818, filed Jun. 7, 1995 and issued as U.S. Pat. No. 5,665,751.

TECHNICAL FIELD

The present invention relates to methods for the treatment of cancer or a viral infection, particularly in human and warm blooded animals containing 2-(2,4-difluorophenyl)-1,3-bis(1H-1,2,4-triazol-1-yl)propan-2-ol, or derivative thereof. The methods may use such a compound in combination with a chemotherapeutic agent and/or a potentiator.

BACKGROUND OF THE INVENTION

Cancers, including leukemia, are the leading cause of death in animals and humans. The exact cause of cancer is not known, but links between certain activities such as smoking or exposure to carcinogens and the incidence of certain types of cancer, such as leukemia and certain tumors has been shown by a number of researchers.

Many types of chemotherapeutic agents have been shown to be effective against cancers, tumors and leukemia, but not all types of cancer and tumor cells respond to these agents. Unfortunately, many of these agents also destroy normal cells. The exact mechanism for the action of these chemotherapeutic agents are not always known.

Despite advances in the field of cancer and leukemia treatments the leading therapies to date are radiation, chemotherapy and bone marrow transplants. Chemotherapeutic approaches are said to fight cancers that are particularly aggressive. Cytocidal or cytostatic agents work best on cancers with large growth factors, i.e., ones whose cells are rapidly dividing. To date, hormones, in particular estrogen, progesterone and testosterone, certain antibiotics produced by a variety of microbes, alkylating agents, and antimetabolites form the bulk of therapies available to oncologists. Ideally, cytotoxic agents that have specificity for leukemia, cancer or tumor cells while not affecting normal cells would be extremely desirable. Unfortunately, none have been found and instead agents that target especially rapidly dividing cells (both diseased and normal) have been used.

Clearly, the development of materials that would target cancer or leukemia cells due to a unique specificity for them would be a breakthrough. Alternatively, materials that were cytotoxic to leukemia or cancer cells while exerting mild effects on normal cells would be desirable. Due to the above-mentioned problems in the art, the present inventor has sought improvements and provides such improvements herein.

HIV and other viral infections are also one leading cause of death. HIV is a disease in which a virus which attacks the body's immune system is replicated in the body. The HIV virus is not easily destroyed nor is there a good mechanism for keeping the host cells from replicating the virus.

Several drugs have been approved for treatment of this devastating disease, including zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), erythropoietin, colony stimulating factors (G-CSF and GM-CSF), non-nucleoside inhibitors, and nucleoside inhibitors. See M. I. Johnston & D. F. Hoth, Science, 260(5112), 1286–1293 (1993) and D. D. Richman, Science, 272(5270), 1886–1888 (1996 An AIDS vaccine (Salk's vaccine) has been tested and several proteins which are chemokines from CD8 have been discovered to act as HIV suppressors. In addition to the above synthetic nucleoside analogs, proteins, and antibodies, several plants and substances derived from plants have been found to have in vitro anti-HIV activity. However, HIV virus is not easily destroyed nor is there a good mechanism for keeping the host cells from replicating the virus.

Thus, medical professionals continue to search for drugs that can prevent HIV infections, treat HIV carriers to prevent them from progressing to full-blown deadly AIDS, and treat the AIDS patient. Accordingly, a material which targets the HIV virus and inhibits viral replication is highly desirable.

Herpes simplex is another viral infection which is difficult to cure. Herpes simplex virus (HSV) types 1 and 2 are persistent viruses that commonly infect humans. HSV type 1 causes oral "fever blisters" (recurrent herpes labialis), and HSV type 2 causes genital herpes, which has become a major venereal disease in many parts of the world. No fully satisfactory treatment for genital herpes currently exists. In addition, although it is uncommon, HSV can also cause encephalitis, a life-threatening infection of the brain. (The Merck Manual, Holvey, Ed., 1972; Whitley, Herpes Simplex Viruses, In: Virology, 2nd Ed., Raven Press (1990)). A most serious HSV-caused disorder is dendritic keratitis, an eye infection that produces a branched lesion of the cornea, which can in turn lead to permanent scarring and loss of vision. Ocular infections with HSV are a major cause of blindness.

Hepatitis is a disease of the human liver. It is manifested with inflammation of the liver and is usually caused by viral infections and sometimes by toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus with a virion size of 42 nm. HCV is a RNA virus with a virion size of 30–60 nm. See D. S. Chen, J. Formos. Med. Assoc., 95(1), 6–12 (1996).

Hepatitis C infects 4 to 5 times the number of people infected with HIV. Hepatitis C is difficult to treat, and it is estimated that there are 500 million people infected with it worldwide (about 15 time those infected with HIV). No effective immunization is currently available, and hepatitis C can only be controlled by other preventive measures such as improvement in hygiene and sanitary conditions and interrupting the route of transmission. At present, the only acceptable treatment for chronic hepatitis C is interferon which requires at least six (6) months of treatment and/or ribavarin which can inhibit viral replication in infected cells and also improve liver function in some people. Treatment with interferon with or without ribavarin, however, has limited long term efficacy with a response rate of about 25%.

Hepatitis B virus infection leads to a wide spectrum of liver injury. Moreover, chronic hepatitis B infection has been linked to the subsequent development of hepatocellular carcinoma, a major cause of death. Current prevention of HBV infection is a hepatitis B vaccination which is therapeutically effective. However, vaccination is not effective in treating those already infected (i.e., carriers and patients). Many drugs have been used in treating chronic hepatitis B and none have been proven to be effective, except interferon.

Treatment of HCV and HBV with interferon has limited success and has frequently been associated with adverse side effects such as fatigue, fever, chills, headache, myalgias, arthralgias, mild alopecia, psychiatric effects and associated disorders, autoimmune phenomena and associated disorders and thyroid dysfunction. Because the interferon therapy has limited efficacy and frequent adverse effects, a more effective regimen for the treatment of these viral infections is needed.

The development of materials that would target HIV infected cells or a range of viruses due to some unique specificity for them would be a breakthrough. Alternatively, materials that were cytotoxic to viruses while exerting mild side effects on normal cells would be desirable.

SUMMARY OF THE INVENTION

Methods for treatment of mammals, and in particular, warm blooded animals and humans, that are affected by cancer or viral infection comprising administering a therapeutically effective amount of 2-(2,4-difluorophenyl)-1,3-bis(1H-1,2,4-triazol-1-yl)propan-2-ol (FLUCONAZOLE®), or derivatives thereof, are provided by the present invention. 2-(2,4-Difluorophenyl)-1,3-bis (1H-1,2,4-triazol-1-yl)propan-2-ol has the formula:

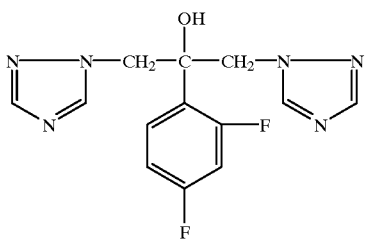

These compositions do not significantly affect healthy cells and are particularly effective against carcinoma, and the influenza virus.

DETAILED DESCRIPTION OF THE INVENTION

A. Definitions

As used herein, "a therapeutically effective amount," means the concentration or quantity or level of the compound of the present invention that can attain a particular medical end, such as control or destruction of cancer cells, virally-infected cells, or viruses without producing unacceptable toxic symptoms. The term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "subject in need thereof," is an animal, preferably a mammal, having cancer or having a viral infection.

As used herein, "cancer" refers to all types of cancers, or neoplasms or benign or malignant tumors. In one embodiment, those cancers that attack normal healthy blood cells or bone marrow are contemplated by the present invention. Preferred cancers for treatment using methods provided herein include sarcoma, carcinoma, lymphoma or leukemia. By "carcinoma" is meant a benign or malignant epithelial tumor and includes, but is not limited to, breast carcinoma, prostate carcinoma, non-small cell lung carcinoma, colon carcinoma, CNS carcinoma, melanoma carcinoma, ovarian carcinoma, or renal carcinoma. A preferred host is a human host.

As used herein, "viruses" includes viruses that cause disease in warm blooded animals including HIV, influenza virus, rhinoviruses, polio virus, hepatitis viruses, herpes, polio myelitis and others known to those of ordinary skill in the art in light of the present disclosure.

As used herein, 2-(2,4-difluorophenyl)-1,3-bis(1H-1,2,4-triazol-1-yl)propan-2-ol or derivative thereof are "compounds of the present invention." Such compounds are further set forth under B infra.

As used herein, "potentiators" are materials that affect the immune system or enhance the effectiveness of the drugs and are further set forth under D herein.

As used herein, "chemotherapeutic agents" includes DNA-interactive agents, antimetabolites, tubulin-interactive agents, hormonal agents and others, such as asparaginase or hydroxyurea and are as further set forth under C infra.

Following long-standing patent law convention, the terms "a" and "an" mean "one or more" when used in this application, including the claims.

B. 2-(2,4-Difluorophenyl)-1,3-bis(1H-1,2,4-triazol-1-YL) propan-2-ol or Derivatives Thereof 2-(2,4-Difluorophenyl)-1,3-bis(1H-1,2,4-triazol-1-yl) propan-2-ol has the following structure:

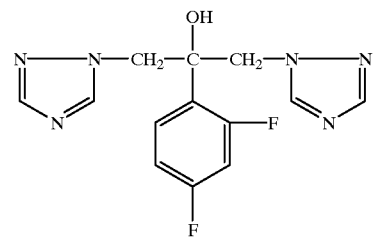

It is prepared according to the method described in U.S. Pat. No. 4,404,216 issued to Richardson (1983). The patent is incorporated by reference herein. As used herein, a "compound of the present invention" is 2-(2,4-difluorophenyl)-1,3-bis(1H-1,2,4-triazol-1-yl)propan-2-ol. Included within the scope of compounds of the present invention are derivatives of the above compound, including the lower carboxylic acid esters of the propanol group, for example, acetyl, propanoyl, butyl, pentyl and hexyl esters. Particularly preferred are the esters of carboxylic acids having less than seven carbons, and most preferably propyl esters. Aryl carboxylic acids such as salicylic acid, benzoic acid, and related acids can also be used to esterify the propanol group. Alkyl ethers having less than 7 carbons are also useful derivatives.

Further, included within the scope of the compound, or derivatives thereof, useful for the present invention are prodrugs. As used herein, a "prodrug" is a drug covalently bonded to a carrier wherein release of the drug occurs in vivo when the prodrug is administered to a mammalian subject. Prodrugs of the compounds of the present invention are prepared by modifying functional groups present in the compounds in such a way that the modifications are cleaved, either in routine manipulation or in vivo, to yield the desired compound. Prodrugs include compounds wherein hydroxy, amine, or sulfhydryl groups are bonded to any group that, when administered to a mammalian subject, is cleaved to form a free hydroxyl, amino, or sulfhydryl group, respectively. Examples of prodrugs include, but are not limited to, acetate, formate, or benzoate derivatives of alcohol or amine functional groups in the compounds of the present invention; phosphate esters, dimethylglycine esters, aminoalkylbenzyl esters, aminoalkyl esters or carboxyalkyl esters of alcohol or phenol functional groups in the compounds of the present invention; or the like.

Pharmaceutically acceptable addition salts of compounds of the present invention are also considered within the scope of derivatives of the present invention and are salts of 2-(2,4-difluorophenyl)-1,3-bis(1H-1,2,4-triazol-1-yl) propan-2-ol with an organic or inorganic acid. Preferred acid addition salts are chlorides, bromides, sulfates, nitrates, phosphates, sulfonates, formates, tartrates, maleates, malates, citrates, benzoates, salicylates, ascorbates, or the like. Such salts may be synthesized from the compound, or derivative thereof, of the present invention that contains a basic or acidic moiety by conventional chemical methods. Generally, such salts may be prepared by reacting a free acid or base form of the compound, or derivative thereof, with a stoichiometric amount of the appropriate base or acid in water or in an organic solvent, or in a mixture of the two; generally, nonaqueous media like ether, ethyl acetate, ethanol, isopropanol, or acetonitrile are preferred. Further suitable salts may be found in *Remington. The Science and Practice of Pharmacy,* 19th ed., Mack Publishing Company, Easton, Pa., 1995, p. 1457.

Pharmaceutically acceptable salts of the compounds or derivatives thereof of the present invention include conventional non-toxic salts or the quaternary ammonium salts of the compounds or derivatives formed, for example, from non-toxic inorganic or organic acids. For example, such conventional non-toxic salts include those derived from inorganic acids such as hydrochloric, hydrobromic, sulfuric, sulfamic, phosphoric, nitric, or the like; and salts prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, or the like. Preferred acid addition salts are chlorides, bromides, sulfates, nitrates, phosphates, sulfonates, formates, tartrates, maleates, malates, citrates, benzoates, salicylates, ascorbates, or the like.

These compounds are part of a generic class of fungicides having the formula:

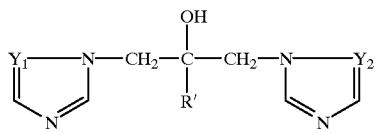

wherein $R^1$ is an optionally-substituted alkyl, cycloalkyl, aryl (2,4-dichlorophenyl) or aralkyl group, and $Y^1$ and $Y^2$ are =CH— or =N—; and salts or metal complexes and ether or esters thereof. While these materials are active against fungus disease, some have been found to be teratogenic. Therefore, those materials which exhibit this teratogenic property are not useful herein.

C. Screening Assays

Screening assays for determining those cancers susceptible to treatment using compounds of the present invention include incubating cell line models representing specific cancers as set forth, for example, by the National Cancer Institute, in the presence and absence of such compounds. Viability of cells may be determined by the MTT assay (Promega Corp., Madison, Wis. 53711), or the SRB (sulforhodamine B) assay (Skehan, et al., *JNCI,* 82:13,1107, 1990). Susceptibility to said compounds exists when viability in the presence of a compound of the present invention is less than viability in the absence of such compound.

Exemplary cell line models representing specific cancers include, but are not limited to, the following:

Non-small cell lung cancer: NCIH23, NCIH324, NCIH522, A549/ATCC, A549(ASC), CALU1, EKVX, NCIHI25M, NCIH226, NCIH520, SKMES1, NCIH322M, NCIH358M, NCIH460, NCIH292, HOP62, HOP18, HOP19, HOP92, LXFL 529, SW1573, LXFS 650L, ML1019, ML1076, ML1045, or UABLG22;

Small cell lung cancer: NCIH69, NCIH146, NCIH82, NCIH524, DMS 114, DMS 273, HOP27, SHP77, or RHOS;

Colon cancer: HT29, HCC2998, HCT116, LOVO, SW1116, SW620, COLO 205, DLD1, WIDR, COLO 320DM, HCT15, CXF 280, KM12, KM20L2, COLO 741, CXF 264L, COLO 746, UABC02, MLI059, CAC02, HT29/PAR, HT29/MDR1, or NB4;

Breast cancer: MCF7, MCF7/ADRRES, ZR751, ZR7530, MDAMB231/ATCC, HS 578T, UISOBCA1, MCF7/ATCC, SKBR3, MDAMB435, MDAN, BT549, T47D, MDAMB231, MAXF 401, BT474, or MDAMB468;

Ovarian cancer: OVCAR3, OVCAR4, OVCAR5, OVCAR8, A2780, IGROV1, SKOV3, OVXF 899, A1336, or ES2;

Leukemia: P388, P3888/ADR, CCRFCEM, CCRFSB, K562, MOLT4, L1210, HL60(TB), RPMI8226, SR, or K562/ADR;

Fibroblast: IMR90, or CCD19LU;

Renal cancer: UO31, SN12C, SN12S1, SN12K1, SN12L1, SN12A1, A498, A704, CAKI1, RXF 393, RXF631, 7860, SW156, TK164, 769P, SS78, ACHN, TK10, RXF 486L, UOK57, or UOK57LN;

Melanoma: LOX IMVI, MALME3M, RPMI7951, SKMEL2, SKMEL5, SKMEL28, SKMEL31, UCSD 242L, UCSD 354L, M14, M19MEL, UACC62, UACC257, MEXF 514L, or UABMEL3;

Prostate cancer: PC3, PC3M, DU145, LNCAP, 1013L, UMSCPI, WIS, JE, RER, MRM, DHM, AG, RB, RVP, FC, WAE, DB/SMC, JCA1, ND1, WMF, TSUPRI, JECA, GDP, T10, WBW, RVP1, or WLL;

CNS cancer: SNB7, SNB19, SNB44, SNB56, SNB75, SNB78, U251, TE671, SF268, SF295, SF539, XF 498, SW 1088, SW 1783, U87 MG, SF767, SF763, A172, or SMSKCNY;.

Bone/muscle: A204/ATCC, OHS, TE85, A673, CHA59, MHM 25, RH18, RH30, or RD; and

Lymphoma: AS283, HT, KD488, PA682, SUDHL7, RL, DB, SUDHL1, SUDHL4, SUDHL10, NUDUL1, or HUT 102.

D. Chemotherapeutic Agents

Chemotherapeutic agents are generally grouped as DNA-interactive agents, antimetabolites, tubulin-interactive agents, hormonal agents, other agents such as asparaginase or hydroxyurea, and agents as set forth in Table 1. Each of the groups of chemotherapeutic agents can be further divided by type of activity or compound. Chemotherapeutic agents used in combination with 2-(2,4-difluorophenyl)-1,3-bis(1H-1,2,4-triazol-1-yl)propan-2-ol and its derivatives of the present invention may be selected from any of these groups but are not limited thereto. For a detailed discussion of the chemotherapeutic agents and their method of administration, see Dorr, et al, *Cancer Chemotherapy Handbook*, 2d edition, pages 15–34, Appleton & Lange (Connecticut, 1994) herein incorporated by reference.

DNA-interactive agents include alkylating agents, e.g. cisplatin, cyclophosphamide, altretamine; DNA strand-breakage agents, such as bleomycin; intercalating topoisomerase II inhibitors, e.g., dactinomycin and doxorubicin); nonintercalating topoisomerase II inhibitors such as, etoposide and teniposde; and the DNA minor groove binder plcamydin, for example.

The alkylating agents form covalent chemical adducts with cellular DNA, RNA, or protein molecules, or with smaller amino acids, glutathione, or similar chemicals. Generally, alkylating agents react with a nucleophilic atom in a cellular constituent, such as an amino, carboxyl, phosphate, or sulfhydryl group in nucleic acids, proteins, amino acids, or in glutathione. The mechanism and the role of these alkylating agents in cancer therapy is not well understood.

Typical alkylating agents include, but are not limited to, nitrogen mustards, such as chlorambucil, cyclophosphamide, isofamide, mechlorethamine, melphalan, uracil mustard; aziridine such as thiotepa; methanesulphonate esters such as busulfan; nitroso ureas, such as carmustine, lomustine, streptozocin; platinum complexes, such as cisplatin, carboplatin; bioreductive alkylator, such as mitomycin, and procarbazine, dacarbazine and altretamine.

DNA strand breaking agents include bleomycin, for example.

DNA topoisomerase II inhibitors include the following intercalators, such as amsacrine, dactinomycin, daunorubicin, doxorubicin (adriamycin), idarubicin, and mitoxantrone; nonintercalators, such as etoposide and teniposide, for example.

A DNA minor groove binder is plicamycin, for example.

Antimetabolites interfere with the production of nucleic acids by one of two major mechanisms. Certain drugs inhibit production of deoxyribonucleoside triphosphates that are the immediate precursors for DNA synthesis, thus inhibiting DNA replication. Certain of the compounds are analogues of purines or pyrimidines and are incorporated in anabolic nucleotide pathways. These analogues are then substituted into DNA or RNA instead of their normal counterparts.

Antimetabolites useful herein include, but are not limited to, folate antagonists such as methotrexate and trimetrexate; pyrimidine antagonists, such as fluorouracil, fluorodeoxyuridine, CB3717, azacitidine, cytarabine, and floxuridine; purine antagonists include mercaptopurine, 6-thioguanine, fludarabine, pentostatin; sugar modified analogs include cyctrabine, fludarabine; and ribonucleotide reductase inhibitors include hydroxyurea.

Tubulin interactive agents act by binding to specific sites on tubulin, a protein that polymerizes to form cellular microtubules. Microtubules are critical cell structure units. When the interactive agents bind the protein, the cell can not form microtubules Tubulin interactive agents include vincristine and vinblastine, both alkaloids and paclitaxel, for example.

Hormonal agents are also useful in the treatment of cancers and tumors. They are used in hormonally susceptible tumors and are usually derived from natural sources. Hormonal agents include, but are not limited to, estrogens, conjugated estrogens and ethinyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, and methyltestosterone.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include, but are not limited to, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include, for example, antiestrogenic agents such as tamoxifen, antiandrogen agents such as flutamide; and antiadrenal agents such as mitotane and aminoglutethimide.

Further agents include the following: hydroxyurea appears to act primarily through inhibition of the enzyme ribonucleotide reductase, and asparaginase is an enzyme which converts asparagine to nonfunctional aspartic acid and thus blocks protein synthesis in the tumor.

Taxol (paclitaxel) is a preferred chemotherapeutic agent.

A listing of currently available chemotherapeutic agents according to class, and including diseases for which the agents are indicated, is provided as Table 1.

TABLE 1

Neoplastic Diseases[1] for which Exemplary Chemotherapeutic agents are Indicated

| Class | Type of Agent | Name | Disease[2] |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan | Multiple myeloma, breast, ovary |

TABLE 1-continued

Neoplastic Diseases[1] for which Exemplary Chemotherapeutic agents are Indicated

| Class | Type of Agent | Name | Disease[2] |
|---|---|---|---|
| | | Chlorambucil | Chronic lymphocytic leukemia, primary macroglobulinemia, Hodgkin's disease, non-Hodgkin's lymphomas |
| | | Estramustine | Prostate |
| | Ethylenimines and Methyl-melamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine | Hodgkin's disease, non-Hodgkin's lymphomas, primary brain tumors, multiple myeloma, malignant melanoma |
| | | Lomustine | Hodgkin's disease, non-Hodgkin's lymphomas, primary brain tumors, small-cell lung |
| | | Semustine | Primary brain tumors, stomach, colon |
| | | Streptozocin | Malignant pancreatic insulinoma, malignant carcinoid |
| | Triazenes | Dacarbazine Procarbazine Aziridine | Malignant melanoma, Hodgkin's disease, soft-tissue sarcomas |
| Antimetabolites | Folic Acid Analogs | Methotrexate Trimetrexate | Acute lymphocytic leukemia, choriocarcinoma, mycosis fungoides, breast, head and neck, lung, osteogenic sarcoma |
| | Pyrimidine Analogs | Fluorouracil Floxuridine | Breast, colon, stomach, pancreas, ovary, head and neck, urinary bladder, premalignant skin lesions (topical) |
| | | Cytarabine Azacitidine | Acute granulocytic and acute lymphocytic leukemias |
| | Purine Analogs and Related Inhibitors | Mercaptopurine | Acute lymphocytic, acute granulocytic, and chronic granulocytic leukemias |
| | | Thioguanine | Acute granulocytic, acute lymphocytic, and chronic granulocytic leukemias |
| | | Pentostatin | Hairy cell leukemia, mycosis fungoides, chronic lymphocytic leukemia |
| | | Fludarabine | Chronic lymphocytic leukemia, Hodgkin's and non-Hodgkin's lymphomas, mycosis fungoides |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | | Vindesine | Vinca-resistant acute lymphocytic leukemia, chronic myelocytic leukemia, melanoma, lymphomas, breast |
| | Epipodophyllo-toxins | Etoposide Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin | Choriocarcinoma, Wilms' tumor, rhabdomyosarcoma, testis, Kaposi's sarcoma |
| | | Daunorubicin | Acute granulocytic and acute lymphocytic leukemias |
| Natural Products | | Doxorubicin 4'-Deoxydoxorubicin | Soft-tissue, osteogenic, and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; Hodgkin's disease, non-Hodgkin's lymphomas |
| | | Plicamycin | Testis, malignant hypercalcemia |
| | | Mitomycin | Stomach, cervix, colon, breast, pancreas, bladder, head and neck |
| | Enzymes | L-Asparaginase | Acute lymphocytic leukemia |
| | Taxanes | Docetaxel | Breast, ovarian |

TABLE 1-continued

Neoplastic Diseases[1] for which Exemplary Chemotherapeutic agents are Indicated

| Class | Type of Agent | Name | Disease[2] |
|---|---|---|---|
| | Taxoids | Paclitaxel | |
| | Biological Response Modifiers | Interferon Alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| | | Tumor Necrosis Factor | Investigational |
| | | Tumor-Infiltrating Lymphocytes | Investigational |
| Miscellaneous Agents | Platinum Coordination Complexes | Cisplatin Carboplatin | Testis, ovary, bladder, head and neck, lung, thyroid, cervix, endometrium, neuroblastoma, osteogenic sarcoma |
| | Anthracened ione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine | Hodgkin's disease |
| | Adrenocortical Suppressant | Mitotane | Adrenal cortex |
| | | Aminoglutethimide | Breast |
| Hormones and Antagonists | Adrenocorticosteroids | Prednisone | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstil-bestrol Ethinyl estradiol | Breast, prostate |
| | Antiestrogen | Tamoxifen | Breast |
| | Androgens | Testosterone Propionate Fluoxymesterone | Breast |
| | Antiandrogen | Flutamide | Prostate |
| | Gonadotropin-releasing hormone analog | Leuprolide Goserelin | Prostate, Estrogen-receptor-positive breast |

[1] Adapted from Calabresi, P., and B. A. Chabner, "Chemotherapy of Neoplastic Diseases" Section XII, pp 1202–1263 in: Goodman and Gilman's The Pharmacological Basis of Therapeutics, Eighth ed., 1990 Pergamin Press, Inc.; and Barrows, L. R., "Antineoplastic and Immunoactive Drugs", Chapter 75, pp 1236–1262, in: Remington: The Science and Practice of Pharmacy, Mack Publishing Co. Easton, PA, 1995.; both references are incorporated by reference herein, in particular for treatment protocols.
[2] Neoplasms are carcinomas unless otherwise indicated.

E. Potentiators

A "potentiator," as used herein, is a material that improves or increases the efficacy of 2-(2,4-difluorophenyl)-1,3-bis(1H-1,2,4-triazol-1-yl)propan-2-ol or a derivative thereof, or that acts on the immune system as an immunomodulator, and is used in combination with a compound of the present invention. One such potentiator is triprolidine or its cis-isomer. Triprolidine is described in U.S. Pat. No. 5,114,951 (1992, the patent is incorporated by reference herein). A further potentiator is procodazole, (also named 1H-benzimidazole-2-propanoic acid, or β-(2-benzimidazole) propionic acid or 2-(2-carboxyethyl)benzimidazole or propazol). Procodazole is a non-specific immunoprotective agent active against viral and bacterial infections and may be used in combination with the compounds set forth herein. Procodazole is effective with 2-(2,4-difluorophenyl)-1,3-bis(1H-1,2,4-triazol-1-yl)propan-2-ol or derivatives thereof in treating cancers, tumors, leukemia or viral infections, and can be combined with one or more therapeutic agents.

Further potentiators include propionic acid, salts thereof, or esters thereof; or antioxidant vitamins such as vitamins A, C, E, or beta-carotene; abacavir; AL-721 (lipid mixture); amprenavir; Amphotericin B methyl ester; Ampligen (mismatched RNA); anti-AIDS antibody; anti-human interferon-á antibody; anti-AIDS antibody, ascorbic acid and derivatives thereof; AS-101 (heavy metal based immunostimulant); azidothymidine; á-interferon; Bropirimine; butylated hydroxytoluene; Ciamexon, Cimetidine; CL-246,738, colony stimulating factors, including GM-CSF; Creme Pharmatex (benzalkonium chloride); CS-82 (5-unsubstituted derivative of Zidovudine); Cyclosporin; D-penicillamine (3-mercapto-D-valine); delavirdine; dextran sulphate; dinitrochlorobenzene; efavirenz; erythropoietin; Foscarnet (trisodium phosphonoformate); fusidic acid; ganciclovir; glucan;

glycyrrhizin, HPA-23 (ammonium-21-tungsto-9-antimonate); human immunevirus antiviral; hyperimmune gamma-globulin, IMREG-1, IMREG-2; indinavir; interferoná; interferon-gamma; interleukin-1 or interleukin-2; isoprinosine; Krestin; LC-9018; lamivudine; lentilart; LF-1695; methionine-enkephalin; Minophagen C; muramyl tripeptide; naltrexone; nelfinavir; Neutropin; nevirapine; Nonoxinol; Ornidyl (eflornithine); non-nucleoside inhibitors of reverse transcriptase; nucleoside analogues (ddA, ddC, ddI, ddT, ddG, AZT, and the like); pentamidine isethionate; Phenytoin; polymannoacetate; Peptide T (octapeptide sequence); protease inhibitors; Ribavirin; Rifabutin (ansamycin); ritonavir; RNA immunomodulator; rsT4 (recombinant soluble T4); saquinavir; shosaikoto and ginseng; SK-818 (germanium-derived antiviral); sodium diethylthiocarbarmate; stavudine; stearic acid derivative; suramin and analogues thereof; thymic humoral factor; TP-5; Thymosin fraction 5 and Thymosin 1; Thymostimulin; TNF (tumor necrosis factor), vitamin B preparations; Trimetrexate; UA001; á-interferon or acyclovir, for example. Other potentiators that may be used in combination with a compound of the present invention include monensin, an antisense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl)ethylenediamine, leucovorin, heparin, N-[4-[(4-fluorphenyl)sulfonly]phenyl] acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, or dimethyl sulfoxide.

A compound, or derivative thereof, of the present invention may be combined with a potentiator and optionally with a therapeutic agent or another antiviral agent in the methods of the present invention.

F. Dosage

Any suitable dosage may be administered in the methods of the present invention. The compound or derivative thereof chosen for a particular application, the carrier and the amount will vary widely depending on the species of the warm blooded animal or human, the type of cancer, or the particular viral infection being treated, and depending upon the effective inhibitory concentrations observed in trial studies. The dosage administered will, of course, vary depending upon known factors, such as the pharmacodynamic characteristics of the particular compound, derivative, or combination and its mode and route of administration; the age, health, or weight of the subject; the nature and extent of symptoms; the metabolic characteristics of the drug and patient, the kind of concurrent treatment; the frequency of treatment; or the effect desired.

Generally a dosage of as little as about 1 milligram (mg) per kilogram (kg) of body mass is suitable, but preferably as little as 10 mg/kg and up to about 10,000 mg/kg may be used. Preferably, a dosage from 10 mg/kg to about 5000 mg/kg is used. Most preferably, the dose is between 250 mg/kg to about 5000 mg/kg. Doses useful in the treatment of cancer or viral infections are 250 mg/kg, 500 mg/kg, 1000 mg/kg, 1500 mg/kg, 2500 mg/kg, 3500 mg/kg, 4000 mg/kg, 5000 mg/kg, or 6000 mg/kg. Any range of doses can be used. Generally, a compound, derivative thereof or combination of the present invention can be administered on a daily basis one or more times a day, or one to four times a week either in a single dose or separate doses during the day. Twice weekly dosing over a period of at least several weeks is preferred, and often dosing will be continued over extended periods of time and possible for the lifetime of the patient. However, the dosage and the dosage regimen will vary depending on the ability of the patient to sustain the desired and effective plasma levels of the compounds of the present invenion, or derivatives thereof, in the blood.

The compound, derivative thereof, or combination, may be micronized or powdered so that it is more easily dispersed and solubilized by the body. Processes for grinding or pulverizing drugs are well known in the art. For example, a hammer mill or similar milling device can be used. The preferred particle size is less than about 100µ and preferably less than 50µ.

Intravenously, the most preferred doses may range from about 1 to about 100 mg/kg/minute during a constant rate infusion.

The dosage for humans is generally less than that used in mice and is typically about 1/12 of the dose that is effective in mice. Thus, if 500 mg/kg was effective in mice, a dose of 42 mg/kg would be used in humans. For a 60 kg man, this dose would be 2520 mg.

The compounds and derivatives thereof of the present invention are generally safe. The $LD_{50}$ is high, about 1500 mg/kg given orally in mice and there are no special handling requirements. The compounds can be given orally, and since they are not very soluble, they are preferably given in tablet form or as a suspension.

The compounds and derivatives thereof of the present invention may be administered in a unit dosage from which may be prepared by any methods known to one of skill in the art in light of the present disclosure. Unit dosages may include from 1 milligram to 1000 milligrams of active ingredient. Preferably the dosage unit will contain from about 10 mg to about 500 mg active ingredient. The active ingredient is generally present in an amount of about 0.5% to about 95% by weight based on the total weight of the dosage unit.

For intravenous use, preferred dosages may range from about 1 to about 10 mg/kg/minute during a constant rate infusion.

A dosage unit may comprise a single compound or mixtures thereof, with other compounds or other cancer- or viral-inhibiting compounds. The dosage unit may comprise diluents, extenders, carriers, liposomes, or the like. The unit may be in solid or gel form such as pills, tablets, capsules and the like or in liquid form suitable for oral, rectal, topical, intravenous injection or parenteral administration or injection into or around the bone marrow. The range and ratio of 2-(2,4-difluorophenyl)-1,3-bis(1H-1,2,4-triazol-1-yl)propan-2-ol or derivative thereof, to chemotherapeutic agent or to potentiator will depend on the type of cancer or viral infection being treated and the particular chemotherapeutic agent or potentiator.

G. Formulations

Formulations of the present invention include the compound of the present invention, 2-(2,4-difluorophenyl)-1,3-bis(1H1,2,4-triazol-1-yl)propan-2-ol, or derivative thereof and, optionally, a chemotherapeutic agent and, optimally, a potentiator generally mixed with a pharmaceutically acceptable carrier.

A "pharmaceutical carrier" is a pharmaceutically acceptable solvent, suspending agent or vehicle for delivering a compound of the present invention to the animal or human. The carrier may be liquid or solid and is selected with the planned manner of administration in mind. A "pharmaceutically acceptable" component is one that is suitable for use with humans and/or animals without undue adverse side effects (such as toxicity, irritation, and allergic response) commensurate with a reasonable benefit/risk ratio.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also preferred carriers.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like.

Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

Exemplary pharmaceutically acceptable carriers and excipients that may be used to formulate oral dosage forms of the present invention are described in U.S. Pat. No. 3,903,297 to Robert, issued Sep. 2, 1975, incorporated by reference herein. Techniques and compositions for making dosage forms useful in the present invention are described in the following references: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms 2nd Edition* (1976).

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound that enhances absorption or penetration of the active ingredient through the skin or other affected areas. Examples of such dermal penetration enhancers include dimethylsulfoxide and related analogues.

The oil phase of an emulsion used to treat subjects in the present invention may be constituted from ingredients known to one of skill in the art in light of the present disclosure. An emulsion may comprise one or more emulsifiers. For example, an oily phase may comprise at least one emulsifier with a fat or an oil, with both a fat and an oil, or a hydrophilic emulsifier may be included together with a lipophilic emulsifier that acts as a stabilizer. Together, the emulsifier(s), with or without stabilizer(s), make up an emulsifying wax, and the wax together with the oil and/or fat make up the emulsifying ointment base that forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, paraffin, straight or branched chain, mono-or dibasic alkyl esters, mineral oil. The choice of suitable oils or fats for the formulation is based on achieving the desired cosmetic properties, the properties required and compatibility with the active ingredient.

Compounds of the present invention may also be administered vaginally, for example, as pessaries, tampons, creams, gels, pastes, foams or spray formulations containing appropriate carriers in addition to the active ingredient. Such carriers are known in the art in light of the present disclosure.

Formulations for rectal administration may be presented as a suppository with a suitable base comprising, for example, cocoa butter or a salicylate.

Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. Extemporaneous injections solutions and suspensions may be prepared from sterile powders, granules and tablets of the kind previously described. Parenteral and intravenous forms may also include minerals and other materials to make them compatible with the type of injection or delivery system chosen.

In general, water, a suitable oil, saline, aqueous dextrose (glucose), or related sugar solutions and glycols such as propylene glycol or polyethylene glycols are suitable carriers for parenteral solutions. Solutions for parenteral administration preferably contain a water soluble salt of the active ingredient, suitable stabilizing agents and, if necessary, buffer substances. Antioxidizing agents, such as sodium bisulfite, sodium sulfite, or ascorbic acid, either alone or combined, are suitable stabilizing agents. Also used are citric acid salts thereof, or sodium EDTA. In addition, parenteral solutions may contain preservatives, such as benzalkonium chloride, methyl- or propyl-paraben, or chlorobutanol. Suitable pharmaceutical carriers are described in Remington, cited supra.

The present invention additionally contemplates administering compounds of the herein described invention for use in the form of veterinary formulations, which may be prepared, for example, by methods that are conventional in the art in light of the present disclosure.

Useful pharmaceutical dosage formulations for administration of the compounds of the present invention are illustrated as follows:

Capsules: A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules: A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets: A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 ml contains 100 mg of finely divided active ingredient, 200 mg of sodium carboxymethyl cellulose, 5 mg of sodium benzoate, 1.0 g of sorbitol solution, U.S.P., and 0.025 ml of vanillin.

Compounds of the present invention may be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

H. Method of Treatment

The method of treatment can be any suitable method which is effective in the treatment of the particular cancer or viral infection that is being treated. Treatment includes administering a therapeutically effective amount of the compounds of the present invention in a form described herein above, to a subject in need of treatment.

Compounds of the present invention can be administered by any means that produces contact of the active agent with the agent's site of action in the body, for example, suitable means including, but not limited to, oral, rectal, nasal, topical (including transdermal, aerosol, buccal or sublingual), vaginal, parenteral (including subcutaneous, intramuscular, intravenous or intradermal), intravesical, or injection into or around the cancer or site of viral infection. They can be administered by any conventional means available for use in conjunction with pharmaceuticals, either as individual therapeutic agents or in a combination of therapeutics. Preferably, compounds of the present invention are administered as a pharmaceutical formulation comprising at least one compound of the present invention, as defined above, together with one or more pharmaceutically acceptable carriers. It can be co-administered in the form of a tablet or capsule, as an agglomerated powder or in a liquid form or as a liposome.

The preferred route will vary with the condition and age of the recipient, virus or cancer being treated nature of the disorder, or severity of disorder. It is believed that oral administration, or parenteral treatment is the preferred method of administering the compounds to subjects in need thereof.

In each of the above-described methods, the administering may be in vivo, or may be ex vivo. In vivo treatment is useful for treating diseases in a mammal, preferably the mammal is a human; and ex vivo treatment is useful for purging body fluids, such as blood, plasma, bone marrow, and the like, for return to the body. Body tissue may be internal or external to an animal body, or, for example, may be the surface skin of the animal.

I. Combination Therapy

Compounds of the present invention may additionally be combined with chemotherapeutic agents, potentiators, or further antiviral compounds to provide a combination therapy. Combination therapy is intended to include any chemically compatible combination of a compound of the present invention with other compounds of the present invention or other compounds outside of the present invention, as long as the combination does not eliminate the activity of the compound of the present invention. For example, one or more compounds of the present invention may be combined with other antiviral agents, potentiators, or chemotherapeutic agents. In certain embodiments of the invention, a compound of the present invention is used in combination with one or more other therapeutic agents, such as anti-inflammatory, anti-viral, anti-fungal, amoebicidal, trichomonocidal, analgesic, anti-neoplastic, antihypertensives, anti-microbial and/or steroid drugs, to treat antiviral infections. In certain preferred embodiments, viral infections are treated with a compound of the presxent invention in combination with one or more of beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), rifampin, clathiromycin, erythropoietin, colony stimulating factors (G-CSF and GM-CSF), nonnucleoside reverse transcriptase inhibitors, nucleoside inhibitors, adriamycin, fluorouracil, methotrexate, asparaginase and combinations thereof. In the case of retroviral infection, a combination therapy with nucleoside analogues such as AZT, nonnucleoside reversal transcriptase inhibitors, TC-3 or protease inhibitors is particularly contemplated by the present invention. In the case of hepatitis, cyclovir, famciclovir or valacyclovir, Ribavirin, interferon or combinations of Ribavirin and interferon or beta globulin is contemplated as a combination therapy. For herpes, a recombinant alpha interferon can be used as a combination therapy. The active agent can be coadministered, for example, in the form of a tablet or capsule, liposome, as an agglomerated powder or in a liquid form.

Combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disorder being treated, the severity of the disorder and the response to the treatment.

In addition to the use of chemotherapeutic agents and potentiators, 2-(2,4-difluorophenyl)-1,3-bis(1H-1,2,4-triazol-1-yl)propan-2-ol or its derivatives can be combined with fungicides, herbicides or other antiviral agents. Preferred herbicides and fungicides include carbendazim, fluoconazole, benomyl, glyphosate and propicodazole.

When the pharmaceutical compositions are used for treatment of viral infection, they can be combined with other anti-viral agents.

J. Pharmaceutical Kits

The present invention also includes pharmaceutical kits useful, for example, for the treatment of cancer or viral infection, that comprise one or more containers containing a pharmaceutical composition comprising a therapeutically effective amount of a compound of the present invention. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

Anti Viral Evaluation With Human Influenza Virus

Female CD (mice Charles River Breeding Laboratories, Portage, Mich.) 5 to 7 weeks old of age at the time of receipt are used. Mice are approximately 6 to 9 weeks old and weigh approximately 20 to 28 grams at the time test initiation. All mice used in the study do not vary in age by more than 10 days. The mice are housed 6 per cage with bedding. The mice are fed rodent diet 5002 (PMI, St. Louis Mo.) adlibitum. Fresh water is supplied to the mice adlibitum.

Human influenza virus, strain AT2/Taiwan/1/64 is used to challenge the mice. The organism is stored at approximately −70° C. Prior to infectious challenge a vial of frozen stock is thawed and diluted to the appropriate concentration in buffered saline solution. The mice are anesthetized with Halothane and the virus challenge dose is administered intra-nasally in volume of 50 microliters.

Test materials are administered at the concentration and volume as provided below. On days 1 through 14, 10 mice per group receive the test articles by oral lavage. Saline control animals (10) receive a comparable volume of saline as compared to the test article-dosed mice. Test article dosing is accomplished at approximately 24 hour intervals. On day 0 approximately 4 hours after the second dosing of test articles or saline, all mice are challenged intra-nasally with an infective dose of virus calculated to produce approximately 90% lethality. Animals are observed daily for 21 days after infectious challenge for mortality or moribundity.

| Test Material | Dose (mg/kg) | Percent Mortality |
| --- | --- | --- |
| Fluconazole | 350 | 0 |
| Fluconazole | 700 | 30% |
| Saline | — | 100% |
| Amantadine | 75 | 0% |

Further Viral Screening Tests

Further types of viral infections may be tested for susceptibility to compounds of the present invention in screening assays known to those of skill in the art to be predictive of in vivo results.

In an in vitro model for influenza, fluconazole did not show activity. Nor was it active in the screening models for in vitro herpes, in vivo herpes, in vitro HIV acute model or in vitro HIV chronic model or in vivo Rhinovirus screening tests.

The National Cancer Institute did not report any testing of this material before 995.

In Vitro Human Tumor Colony Forming Units Test

Solid tumors removed from patients are minced into 2 to 5 mm fragments and immediately placed in McCoy's Medium 5A plus 10% heat inactivated newborn calf serum lus 1% penicillin/streptomycin. Within 4 hours, these solid tumors are mechanically disassociated with scissors, forced through No. 100 stainless steel mesh, through 25 gauge needles, and then washed with McCoys medium as described above. Ascitic, pleural, pericardial fluids and bone marrow are obtained by standard techniques. The fluid or marrow is placed in sterile containers containing 10 units of preservative free heparin per ml. of malignant fluid or marrow. After centrifugation at 150× g for 10 minutes, the cells are harvested and washed with McCoy's medium plus 10% heat inactivated calf serum. The viability of cell suspensions is determined on a hemocytometer with trypan blue.

Cells to be cloned are suspended in 0.3% agar in enriched CMRL1066 supplemented with 15% heat inactivated horse serum, penicillin (100 units/ml), streptomycin (2 mg/ml), glutamine (2 mM ), insulin (3 units/ml), asparagine (0.6 mg/ml), and HEPES buffer (2 mM ). For the continuous exposure test each compound is added to the above mixture. Cells are placed in 35 mm petri dishes in a top layer of agar over an underlayer of agar to prevent growth of fibroblasts. Three plates are prepared for each data point. The plates are placed in a 37° C. incubator, and are removed on day 14 for counting of the number of colonies in each plate. The number of colonies (defined as 50 cells) formed in the 3 compound treated plates is compared to the number of colonies formed in the 3 control plates, and the percent colonies surviving at the concentration of compound can be tabulated. Three positive control plates are used to determine survival rate. Orthosodium vanadate at 200 µg/ml is used as the positive control. If there is <30% cells in the positive control when compared to the untreated control, the test is evaluated.

At concentrations of 0.5 and 5.0 µg/ml in a continuous exposure experiment or single dose experiment Fluconazole was not effective (0/3 and 0/13 respectively) against tumors. At concentration of 50.0 µg/ml in a continuous exposure experiment Fluconazole was effective against lung, non-small cell, and ovarian cancers particularly. Over all 4/13 had <50% survival.

The human tumor cloning system provided by this study is known by those of skill in the art as providing in vitro predictive assays for selecting an appropriate anticancer agent for an individual patient's cancer.

Combination of Fluconazole With a Chemotherapeutic Agent

In an in vivo mouse model for murine melanoma (B16) fluconazole was tested alone and in combination with adriamycin (doxorubicin) at various doses. The results are summarized below:

| Fluconazole mg/kg dose | Adriamycin mg/kg dose | % Increase in survival time relative to control (100%) | Toxic deaths | Survivors in cancer model | % Body weight change |
| --- | --- | --- | --- | --- | --- |
| 700 | 0 | 120 | 0 | 0 | −1 |
| 700 | 2 | Cures | 0 | 6/6 | +3 |
| 700 | 3 | 286 | 0 | 7/8 | −2 |
| 700 | 4 | 205 | 0 | 9/10 | −3 |
| 350 | 0 | 116 | 0 | 0 | +6 |
| 350 | 2 | 298 | 0 | 8/10 | +2 |
| 350 | 3 | Cures | 0 | 10/10 | +3 |
| 350 | 4 | 174 | 0 | 9/10 | −2 |
| 175 | 0 | 117 | 0 | 0 | +6 |
| 175 | 2 | 230 | 0 | 7/10 | +4 |
| 175 | 3 | 224 | 0 | 9/10 | +6 |
| 175 | 4 | 280 | 0 | 8/10 | −2 |
| 0 | 0 | 100 | 0 | 0 | +9 |
| 0 | 2 | 300 | 0 | 6/10 | +9 |
| 0 | 3 | 280 | 0 | 8/10 | +4 |
| 0 | 4 | Cures | 0 | 10/10 | +0.1 |

These data demonstrate that cures occurred at a dose of 4 mg/kg adriamycin in the absence of fluconazole, but at a concentration of 3 mg/kg in the presence of 350 mg/kg fluconazole, and at 2 mg/kg in the presence of 700 mg/kg fluconazole. Therefore, a combination of fluconazole and a chemotherapeutic agent provides an enhanced therapeutic activity, thereby allowing for use of a lower amount of chemotherapeutic agent.

Methods disclosed and claimed herein can be made and executed without undue experimentation in light of the present disclosure. While the methods of this invention have been described in terms of preferred embodiments, it will be apparent to those of skill in the art that variations may be applied to the composition, methods and in the steps or in the sequence of steps of the method described herein without departing from the concept, spirit and scope of the invention. Such similar substitutes and modifications apparent to those skilled in the art are deemed to be within the spirit, scope and concept of the invention as defined by the appended claims.

What is claimed is:

1. A method of treating a viral infection in a subject in need thereof comprising administering to the subject a therapeutically effective amount of a combination of a viral infection-treating effective amount of a compound when in the combination, the compound selected from the group consisting of 2-(2,4-difluorophenyl)-1,3-bis(1H-1,2,4-triazol-1-yl) propan-2-ol, a derivative thereof selected from the group consisting of a lower carboxylic acid ester, an aryl carboxylic acid ester, and an alkyl ether having from less than 7 carbon atoms; and a mixture thereof; and a viral infection-treating effective amount of an antiviral agent when in the combination.

2. The method of claim 1 wherein from 1 mg/kg body weight to about 1000 mg/kg of the compound is administered.

3. The method of claim 1 wherein the compound and the antiviral agent are administered, individually or in combination; orally, enterically, intravenously, peritoneally, or by injection.

4. A method of treating an influenza infection in a subject in need thereof comprising administering to the subject a therapeutically effective amount of a combination of an influenza infection-treating effective amount of a compound when in the combination, the compound selected from the group consisting of 2-(2,4-difluorophenyl)-1,3-bis(1H-1,2,4-triazol-1-yl) propan-2-ol, a derivative thereof selected from the group consisting of a lower carboxylic acid ester, an aryl carboxylic acid ester, and an alkyl ether having from less than 7 carbon atoms; and a mixture thereof; and an influenza infection-treating effective amount of an antiviral agent when in the combination.

5. The method of claim 4 wherein from 1 mg/kg body weight to about 1000 mg/kg of the compound is administered.

6. The method of claim 4 wherein the compound and the antiviral agent are administered, individually or in combination; orally, enterically, intravenously, peritoneally, or by injection.

* * * * *